US010718694B2

(12) United States Patent
Gupta et al.

(10) Patent No.: US 10,718,694 B2
(45) Date of Patent: Jul. 21, 2020

(54) COUNTERSTAINS FOR A BIOLOGICAL SAMPLE

(71) Applicant: Marc Key, Ojai, CA (US)

(72) Inventors: Bipin Gupta, Pleasanton, CA (US); Marc Key, Ojai, CA (US)

(73) Assignees: Diagnostic BioSystems, Pleasanton, CA (US); Marc Key, Ojai, CA (US)

( * ) Notice: Subject to any disclaimer, the term of this patent is extended or adjusted under 35 U.S.C. 154(b) by 29 days.

(21) Appl. No.: 15/478,959

(22) Filed: Apr. 4, 2017

(65) Prior Publication Data

US 2017/0299482 A1 Oct. 19, 2017

Related U.S. Application Data

(60) Provisional application No. 62/324,204, filed on Apr. 18, 2016.

(51) Int. Cl.
*G01N 1/30* (2006.01)
*G01N 33/58* (2006.01)

(52) U.S. Cl.
CPC ............. *G01N 1/30* (2013.01); *G01N 33/582* (2013.01); *G01N 2001/302* (2013.01)

(58) Field of Classification Search
None
See application file for complete search history.

(56) References Cited

U.S. PATENT DOCUMENTS

| 2013/0044933 A1* | 2/2013 | Kenny | G01N 21/643 |
| | | | 382/133 |
| 2015/0024405 A1* | 1/2015 | May | G01N 33/5306 |
| | | | 435/7.9 |

OTHER PUBLICATIONS

Zieba, A., et al., Bright-Field Microscopy Visualization of Proteins and Protein Complexes by In Situ Proximity Ligation with Peroxidase Detection. Clinical Chemistry 56:1, pp. 99-110 (2010).
Zeeuwen, P.L.J.M., et al., Evidence that unrestricted legurnain activity is involved in disturbed epidermal cornification in cystatin M/E/ deficient mice, Human Molecular Genetics. 2004. vol. 13, No. 10, pp. 1069-1079, Mar. 25, 2004, DOI:10.1093/hmg/ddh115.
Rosa, I., et al., Morphological evidence of telocytes in human synovium, Nature Scientific Reports, 8:3581 (2018), DOI:10.1038/s41598-018-22067-5.
Fonseca, R., et al., Genomic abnormalities in monoclonal gammopathy of undetermined significance, Blood, Aug. 15, 2002, vol. 100. No. 4, pp. 1417-1424.
Feng, R., et al., Turn-on fluorescent probes that can light up endogenous RNA in nucleoli and cytoplasm of living cells under a two-photon microscope, Royal Society of Chemistry Advances, 2017, vol. 7, pp. 16730-16736.
Schmued, L.C., et al., Some Fluorescent Counterstains for Neuroanatomical Studies, The Journal of Histochemistry and Cytochemistry, vol. 30, No. 2. pp. 123-128 (1982).
Guo, Yi-He. et al., Caveolin-1-dependent apoptosis induced by fibrin degradation products, Blood, Apr. 30, 2009. vol. 113, No. 18, pp. 4431-4439.
Stallings, N.R., et al., Development of a Transgenic Green Fluorescent Protein Lineage Marker for Steroidogenic Factor I, Molecular Endocrinology 16(10):2360-2370, doi:10.1210/me.2002-0003.
Pratscher, J., et al., Application of Recognitiion of Individual Genes-Fluorescence In Situ Hybridization (RING-FISH) to Detect Nitrite Reductase Genes (nirK) of Denitrifiers in Pure Cultures and Environmental Samples, Applied and Environmental Microbiology, Feb. 2009, pp. 802-810, vol. 75, No. 3, doi:10.1128/AEM.01992-08.
Ito, I. et al., Increased Uptake of Liposomal-DNA Complexes by Lung Metastases Following Intravenous Administration, Molecular Therapy, vol. 7, No. 3, pp. 409-417, Mar. 2003, doi:10.1016/S1525-0016(03)00004-2.
Lee, Chung-Yin, et al., Bone Marrow Cells in Murine Colitis; Multi-Signal Analysis Confirms Pericryptal Myofibroblast Engraftment without Epithelia Involvement. PLos ONE, Oct. 2011, vol. 6, Issue 10, pp. 1-13, e26082.
Schliekelman, M.J., et al., Thy-1+ Cancer-associated Fibroblasts Adversely Impact Lung Cancer Prognosis, Nature Scientific Reports, 7:6468, DOI:10.1038/s41598-017-06922-5, pp. 1-12.

* cited by examiner

*Primary Examiner* — Susan M Hanley
(74) *Attorney, Agent, or Firm* — Patentfile, LLC; Bradley C. Fach; Steven R. Kick (57) ABSTRACT

The present disclosure relates to counterstains for staining a biological sample on a single slide in preparation for microscopic examination. The counterstains are used to analyze the sample on the single slide using both brightfield and fluorescent illumination. The counterstains can identify both morphological details and molecular structures within the cells contained in the sample. The counterstains can be used in conjunction with other molecular stains.

3 Claims, 4 Drawing Sheets

COUNTERSTAINS FOR A BIOLOGICAL SAMPLE

CROSS REFERENCE TO RELATED APPLICATION

This application claims the benefit of U.S. Provisional Application No. 62/324,204, filed Apr. 18, 2016, entitled COUNTERSTAIN FOR BIOLOGICAL SAMPLES, which is herein incorporated by reference in its entirety for all purposes.

INTRODUCTION

To reveal both morphological details and molecular structures within a biological specimen, two different types of illumination methods are required, brightfield illumination and fluorescence illumination. These two different illumination methods require the use of stains that are not compatible with each other, resulting in the requirement that two separate serial sections of a specimen are stained. For example, one serial section on a first slide stained with a fluorescence stain, and another serial section on a second slide stained with a brightfield stain. A microscopist then mentally reconstructs the two images to determine which cells in the specimen exhibit an altered molecular structure. This mental process can be difficult and can result in error and possibly an incorrect diagnosis.

BACKGROUND OF THE DISCLOSURE

Currently, methods of staining biological samples to obtain both morphological and molecular details are based on two types of illumination, fluorescence illumination and brightfield illumination. Brightfield illumination utilizes stains specifically developed to provide morphological details, such as cell type or disease state. However, these morphological stains do not provide information at the molecular level. To remedy this, fluorescent illumination methods utilize stains specifically developed to provide information at the molecular level. For example, fluorescence stains are useful for examining alterations in a cell at the deoxyribonucleic acid (DNA) level. However, fluorescence stains do not provide morphological information required to identify cell type or disease state. Therefore, a combination counterstain used to stain a biological sample that would allow examination by both fluorescence illumination and brightfield illumination on the same microscope slide would be very useful.

Typically, fluorescence stains and brightfield stains are not combined on the same microscope slide because the two methods are incompatible with each other. When a fluorescence stain is examined under brightfield illumination no staining is observed. Likewise, when brightfield stains are examined by fluorescence illumination either no staining is observed or high background staining, without specific staining is observed.

Current attempts to combine these two staining methods have been ineffective, because the counterstains used for brightfield illumination exhibit unwanted characteristics such as quenching, background, and interference when examined by fluorescence. The usefulness of combining these two staining methods has been recognized and certain work-around methods have been developed.

The most commonly used work-around method involves the preparation of two microscope slides from the same biological sample. From a typical biological sample, multiple microscope slides can be prepared. Typically, the biological sample is cut into thin tissue slices of approximately 4μ, and each slide is affixed to a microscope slide. When these 4μ sections are kept in order and sequentially laid onto a series of microscope slides, the slides are said to be serial sections meaning that the slides are ordered in the same way that the tissue was ordered in the biological sample. The implication is that tissues mounted on serial sections do not vary greatly from each other. They vary only by 4μ, which is less than the diameter of a single cell. Therefore, serial sections are considered to be nearly identical to each other. Thus, it is possible to stain a first section on a first slide with a morphological stain and a serial section on a second microscope slide with a molecular stain. The first slide can be examined by brightfield illumination and the cell type or disease state can be identified. The second slide is then examined by fluorescence illumination and molecular alterations are identified. The microscopist will then mentally reconstruct the two images to determine which cells are exhibiting the altered molecular state. However, the mental process of reconstructing two images can be difficult and result in error. Furthermore, the requirements of staining two different slides make this method more time consuming and expensive compared with staining a single slide using a combined stain.

Therefore, it would be advantageous to be able to combine both brightfield and fluorescence stains within a single slide. By combining the information obtained from both stains on a single slide the investigator can determine both the cell type and specific molecular alterations associated with that cell. For example, a brightfield stain provides the investigator with critical morphological information such that the specific cell type (for example, cancerous) can be identified, and fluorescence examination allows the investigator to observe specific molecular alterations (for example, a molecular marker) within the cell.

SUMMARY OF THE DISCLOSURE

Disclosed herein are counterstains for use in staining one section of a biological specimen on a slide, wherein the one section is analyzed by microscopic analysis using both brightfield and fluorescent illumination. The disclosed counterstains comprise a fluorescent counterstain and a brightfield counterstain.

In one embodiment, the fluorescent counterstain comprises a compound of formula V or VI and the brightfield counterstain comprises a compound of formula XIV. In another embodiment, the fluorescent counterstain comprises a compound of formula V or VI and the brightfield counterstain comprises a compound of formula XV or XVI. In one embodiment, the fluorescent counterstain comprises a compound of formula XI, XII, or XIII, and the brightfield counterstain comprises a compound of formula XV or XVI.

In other embodiments, the fluorescent counterstain comprises a compound of formula I, II, III, IV, V, VI, VII, VIII, IX, X, XI, XII, or XIII.

In other embodiments, the fluorescent counterstain comprises $C_{25}H_{24}N_6O \cdot 3HCl$; $C_{27}H_{28}N_6O \cdot 3HCl$; $C_{27}H_{28}N_6O \cdot 3HCl \cdot xH_2O$, wherein x is 0, or greater than 0; $C_{27}H_{29}N_7 \cdot 3HCl$; $C_{24}H_{29}N_3O_{12}S_2$; $C_{24}H_{27}N_3O_{12}S_2$; $C_{16}H_{15}N_5 \cdot 2C_3H_6O_3$; or $C_{16}H_{15}N_5 \cdot 2HCL$.

In other embodiments, the fluorescent counterstain comprises 2'-(4-Ethoxyphenyl)-6-(4-methyl-1-piperazinyl)-1H, 3'H-2,5'-bibenzimidazole; 2-[2-(4-Hydroxyphenyl)-6-benzimidazoyl]-6-(1-methyl-4-piperazyl)-benzimidazole, 3HCl; 2'-(4-Hydroxyphenyl)-5-(4-methyl-1-piperazinyl)-2,5'-bi (1H-benzimidazole) trihydrochloride, 2-[2-(4-Hydroxyphenyl)-6-benzimidazoyl]-6-(1-methyl-4-piperazyl) benzimidazole trihydrochloride; 2'-(4-hydroxyphenyl)-5-(4-methyl-1-piperazinyl)-2,5'-bi-1H-benzimidazole trihydrochloride hydrate; 2-(4-Ethoxyphenyl)-5-(4-methyl-1-piperazinyl)-2,5-bi-1H-benzimidazole trihydrochloride; N,N-Dimethyl-4-[5-(4-methyl-1-piperazinyl)[2,5'-bi-1H-benzimidazol]-2'-yl]benzenamine trihydrochloride; Xanthane (2,1,9-def) isoquinolinedisulfonic acid, 2-(2-hydroxyethyl)-1,3-dioxo-, bis (2-ethanolamine) salt; 2-phenylindole; 4',6-Diamidino-2-phenylindole dihydrochloride; 2-(4-Amidinophenyl)-6-indolecarbamidine dihydrochloride; 4',6-Diamidino-2-phenylindole, dilactate; or 4',6-Diamidino-2-phenylindole dihydrochloride; 2-(4-Amidinophenyl)-1H-indole-6-carboxamidine, 2HCl; or 2-(4-Carbamimidoylphenyl)-1H-indole-6-carboximidamide, 2HCl; or the brightfield counterstain comprises a compound of formula XIV, XV, XVI, or XVII; or the brightfield counterstain comprises C34H24N6Na4O16S4; C17H18ClN3O4; C17H17N3O4; or C15H14ClN3O4; or the brightfield counterstain comprises 6,6'-[(3,3-Dimethoxy[1,1'-biphenyl]-4,4'-diyl)bis(azo)]bis[4-amino-5-hydroxy-1,3-napthalenedisulphonic acid] tetrasodium; 1-carbamoyl-7-(diethylamino)-3,4-dihydroxyphenoxazin-5-ium chloride; 7-(diethylamino)-3,4-dioxo-4,10-dihydro-3h-phenoxazine-1-carboxamide; or 7-(diethylamino)-4-hydroxy-3-oxophenoxazin-10-ium-1-carboxamide.

In other embodiments, the ratio of fluorescent counterstain to brightfield counterstain is about 1:1, about 1:5, about 1:10, about 1:20, about 1:30, about 1:40, about 1:50, about 1:60, about 1:70, about 1:80, about 1:90, or about 1:100.

In some embodiments, the brightfield counterstain used to make the counterstain is at a concentration of about 10 mg/ml to about 50 mg/ml, or about 1 mg/ml to about 50 mg/ml.

In other embodiments, the fluorescent counterstain used to make the counterstain is at a concentration of about 2.5 ug/ml to about 80 ug/ml, or about 1 ug/ml to about 100 ug/ml.

In yet other embodiments, the combined counterstain (brightfield and fluorescent) has a pH of about 3+/−1 pH unit to about 7.5+/−1 pH unit, or about 2.0+/−1 pH unit to about 8.0+/−1 pH unit.

In some embodiments, the counterstain has an emission spectrum of about 400 nm to about 700 nm, or an emission spectrum about 400 nm to about 550 nm.

In one embodiment, the counterstain is used as a nuclear counterstain by brightfield illumination, has no fluorescence at a reserved emission wavelength in a green spectrum of about 500 nm to about 600 nm, has no fluorescence at a reserved emission wavelength in a red spectrum of about 600 nm to about 700 nm, has no background fluorescence, and has no interference of a signal within the reserved emission wavelengths.

In another embodiment, a compound of formula (V) or formula (VI) and a compound of formula (XIV) are combined to make the counterstain, and the concentration of the compound of formula (V) or (VI) is about 2.5 ug/ml to about 80 ug/ml, or about 1.0 ug/ml to 100 ug/ml, and the concentration of the compound of formula (XIV) is about 10 mg/ml to about 50 mg/ml or 1 mg/ml to about 50 mg/ml.

In one embodiment, a compound of formula (V) or formula (VI) and a compound of formula (XV) or formula (XVI) are combined to make the counterstain, and the concentration of a compound of formula (V) or (VI) is about 2.5 ug/ml to about 80 ug/ml, or about 1.0 ug/ml to 100 ug/ml, and the concentration of a compound of formula (XV) or formula (XVI) is about 10 mg/ml to about 50 mg/ml, or 1 mg/ml to about 50 mg/ml.

In yet another embodiment, a compound of formula (XI), formula (XII), or formula (XIII) and a compound of formula (XV) or formula (XVI) are combined to make the counterstain, and the concentration of a compound of formula (XI), formula (XII), or formula (XIII) is about 2.5 ug/ml to about 80 ug/ml, or about 1.0 ug/ml to 100 ug/ml, and concentration of the compound of formula (XV) or formula (XVI) is about 10 mg/ml to about 50 mg/ml, or 1 mg/ml to about 50 mg/ml.

Also provide herein are methods of staining one section of a biological specimen on a slide, wherein the section is analyzed by microscopic analysis using both brightfield and fluorescent illumination, comprising: a) obtaining a section comprising one or more cells; b) contacting the section with a counterstain for a time sufficient to produce a stain; c) analyzing the section using a microscope that has both brightfield and fluorescent illumination; d) turning the microscope to brightfield illumination and observing a morphological detail of the section; and e) turning the microscope to fluorescent illumination and observing a molecular structure of the section. In another embodiment, step (e) is performed before step (d).

In other embodiments, upon brightfield illumination of the biological specimen on a slide, a nucleus of a cell is observed; a cell type is observed; a cancerous or precancerous cell is observed; or a disease state is observed or not.

In other embodiments, upon fluorescent illumination of the biological specimen on a slide, one or more molecular structures of a cell is either observed or not; the molecular structure is a molecular marker, a cancer marker, HER2 gene, a chromosome, or chromosome 17; an alteration in the cell's deoxyribonucleic (DNA) is either observed or not; or an alteration in the cell's ribonucleic (RNA) is either observed or not. In other embodiments, the observation is by a person's eyes or the observation is a digital image. Also, provided herein are counterstains useful in the disclosed methods.

In one embodiment, a counterstain comprising, Hoechst 33342 at a concentration of about 1.0 ug/ml to about 100 ug/ml and Chicago Sky Blue at a concentration of about 1 mg/ml to about 50 mg/ml at a ratio of about 1:1 and a pH of about 5.0 to about 7.0+/−1 pH unit is disclosed. In another embodiment, a counterstain comprising, Hoechst 33342 at a concentration of about 1.0 ug/ml to about 100 ug/ml and Celestine Blue at a concentration of about 1 mg/ml to about 50 mg/ml at a ratio of 1:1 and a pH of about 5.0 to about 7.0+/−1 pH unit is disclosed.

BRIEF DESCRIPTION OF THE DRAWINGS

These and other features, aspects, and advantages of the present disclosure will become better understood with regard to the following description, appended claims and accompanying figures where:

FIG. 1, right-hand panel shows the same tissue sample as the left-hand panel under fluorescence illumination.

FIG. 2, right-hand panel shows the same tissue sample as the left-hand panel under brightfield illumination (low power).

FIG. 3, right-hand panel shows the same tissue sample as FIG. 2 right-hand panel under brightfield illumination (high power).

FIG. 4, right-hand panel (top and bottom) shows the same tissue sample as the left-hand panel under fluorescence illumination.

DETAILED DESCRIPTION OF THE DISCLOSURE

The following detailed description is provided to aid those skilled in the art in practicing the present disclosure. Even so, this detailed description should not be construed to unduly limit the present invention as modifications and variations in the embodiments discussed herein can be made by those of ordinary skill in the art without departing from the spirit or scope of the present inventive discovery.

As used in this disclosure and the appended claims, the singular forms "a", "an" and "the" include a plural reference unless the context clearly dictates otherwise. As used in this disclosure and the appended claims, the term "or" can be singular or inclusive. For example, A or B, can be A and B.

Ranges

As disclosed herein, a number of ranges of values are provided. It is understood that each intervening value, to the tenth of the unit of the lower limit, unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither, or both limits are included in the smaller ranges is also encompassed within the invention, subject to any specifically excluded limit in the stated range. Where the stated range includes one or both of the limits, ranges excluding either or both of those included limits are also included in the invention.

About

The term "about" generally refers to plus or minus 10% of the indicated number. For example, "about 10%" may indicate a range of 9% to 11%, and "about 1" may mean from 0.9-1.1.

Specimen/Sample

The words "specimen" and "sample" are used interchangeably throughout the disclosure. A specimen can be a biological specimen. A specimen can be one or more cells, a mixture of different types of cells, or a population of cells. A specimen can comprise eukaryotic or prokaryotic cells or a mixture of both. A specimen, such as a group of cells, can be grown directly on a surface suited for cell culture (e.g. a tissue culture dish) or loose cells can be applied to a surface, for example, a microscope slide. A specimen can be a tissue sample or a portion or slice of a tissue sample. A specimen can be embedded in a matrix, such as paraffin, or may be freshly frozen after collection from a mammal (e.g. human or animal).

Staining

Staining is a technique used in microscopic analysis to enhance contrast in the microscopic image. Stains and dyes can be chemical compounds or biological molecules. A stain or dye can be tagged, conjugated to, or be labeled with another chemical compound. Stains and dyes are often used to highlight structures in biological tissue samples to define and examine particular tissue structures, cell populations, or organelles within individual cells. Stains and dyes may also be specific to particular DNA, proteins, lipids, or carbohydrates present in the specimen, and help to determine the presence or absence, or the quantity of the particular species of interest.

The term "staining" refers to a formation of specific binding interaction between the stains or the dyes to the species of interest. For example, a staining may occur when a biomarker, such as an antibody, specifically binds to a protein or an antigen; when a nucleic acid binds to a DNA or RNA sequence; or when a chemical compound that specifically recognizes the nucleus of a cell producing a visible color upon the subsequent contact of a substrate.

Dyes/Stains

The terms "dye" and "stain" can be used interchangeably throughout the disclosure. A dye/stain can also be a chromogen.

Dyes demonstrate an affinity for molecules or organisms within cells and tissues. For example, a dye (stain) can be specific to connective tissue, erythrocytes, mitochondria, nucleic acids, collagen, reticulum, muscle, plasma, nuclei, bacteria, nerve cells, liver cells, cell walls, pituitary cells, reticulum, bone, cartilage, pancreatic cells, marrow cells, cytoplasm, parasites, keratin, or any portion or combination of any of the above.

The affinity of dyes for elements that are present in a cell or tissue is affected by several factors: the structure of the dye molecule; the shape of the dye molecule; the charge distribution of the dye; and solvent characteristics. Stains can be used on fixed, or non-living cells.

Contacting

Contacting, for example, a stained specimen with a stain, dye, or counterstain, can be by submerging, incubating, applying, soaking, pouring, or layering the stained specimen with the stain, dye, or counterstain. Contacting a stained specimen with a counterstain, as disclosed herein, can be for any period of time sufficient to stain the specimen. For example, about 1 to 5 minutes, or 5 minutes to 20 minutes, or 20 minutes or more.

Microscopic Analysis

The term "microscopic analysis" refers to techniques that require a microscope, an instrument or a system that are capable of acquiring data and/or images for analysis. It may be a stand-alone bright-field or fluorescent microscope, a cell imager, a spectrometer, a manual or automated slide stainer and scanner.

The biological specimens can be used in immunological methods, such as immunohistochemistry assays (IHC) and immunocytochemistry assays (ICC). The biological specimens can also be used for in situ hybridization assays (ISH), fluorescent in situ hybridization (FISH) assays, and enzyme-linked immunosorbent assays.

Counterstains

A counterstain implies that it is a secondary stain that is useful in contrasting a first stain. In examination of cells within biological samples it is frequently useful to perform a first stain, such as a specific molecular stain, and then a counterstain (second stain) to provide additional morphological information regarding those cells. Frequently the counterstain of choice for examination of biological samples is a nuclear counterstain which stains the nucleus of each cell a specific color that can be visualized microscopically. This allows the microscopist to observe each individual cell within the biological sample.

Nuclear Counterstains

Nuclear counterstains have the following characteristics: a nuclear counterstain will stain the nucleus of a cell within a biological sample; a nuclear counterstain will allow microscopic examination and provide useful morphological information to the microscopist; and a nuclear counterstain will allow a trained microscopist, such as a pathologist to make an identification as to the tissue type and a diagnosis as to the disease state. These characteristics along with other characteristics of nuclear counterstains are discussed herein.

The nuclear counterstain must be able to stain the nucleus of cells within a biological sample without staining other elements of the cells or tissues. The resulting image would show a colored nucleus. Each nucleus identifies the presence of a single cell. The nuclear counterstain will impart a specific color to the nucleus. In standard histological practices the hematoxylin nuclear counterstain is preferred as this counterstain imparts a blue color to the stained nucleus.

In addition to hematoxylin other blue counterstains such as crystal violet, methylene blue, methyl blue, toluidine blue, alcian blue can be used. Other colors can also be used such as methyl green which imparts a green stain and Nuclear Fast Red which imparts a red stain.

Nuclear counterstains, such as those disclosed herein, typically, have the ability to bind to DNA which is found in the nucleus of cells. This binding causes the nucleus of the cell to become visible when examined by brightfield illumination (microscopy).

Brightfield illumination is the most common light source for standard histological examination. It is a mixture of wavelengths that comprise visible light and is similar to the light emitted from a standard light bulb. In contrast fluorescence illumination uses specific wavelengths of light for illumination. It is more complex and requires light sources and filters that emit and transmit light of defined wavelengths. Some microscopes have the ability to utilize either brightfield light or fluorescent light depending on the microscope configuration.

All of the above mentioned nuclear counterstains produce their specific colors when viewed under brightfield illumination, but none of these stains can be used in fluorescence microscopy for one or more of the following reasons: 1) they produce their own fluorescence at undesired wavelengths, 2) they produce background fluorescence which obscures the desired fluorescence signals, and 3) they interfere with the desired fluorescence signal by quenching, that decreases the brightness of the desired signals.

Brightfield Examination (Illumination)

Brightfield examination has the following characteristics: a biological sample stained with a nuclear counterstain may be examined under brightfield illumination; this type of illumination uses white light in the visible spectrum; a nuclear counterstain will absorb certain wavelengths of light and reflect other wavelengths of light to produce a specific color to the stained nuclei; a stained nuclei can then be examined by a trained microscopist, such as a pathologist, to identify certain cell types and to diagnose certain disease states; examination of a stained biological sample is useful for identifying various cell types in complex tissues comprised of multiple cell types; and brightfield examination is useful for identifying disease states within tissues, such as cancer or other pathological conditions. These characteristics along with other characteristics of brightfield examination are discussed herein.

As mentioned above, brightfield illumination uses standard white light of the visible spectrum commonly emitted from a halogen light source. Under brightfield illumination the biological sample will be uniformly white or transparent except for those areas of the sample that have taken up a stain. In the case of a nuclear counterstain, each nucleus will appear colored on a white or transparent background. The specific color of the nuclei will be determined by the properties of the counterstain, and in most cases, is typically blue.

The stained nucleus imparts important morphological details that can be used by a trained microscopist to identify the cell type and disease state. For example, a pathologist can make the diagnosis of cancer from brightfield examination of a stained biological sample.

Fluorescence Examination (Illumination)

Fluorescence examination has the following characteristics: fluorescence examination focuses light of a specific wavelength (an excitation wavelength) on a biological sample; a fluorescent object absorbs the illuminating wavelength and emits light at a different wavelength (an emission wavelength); fluorescent staining methods are frequently used to stain specific molecular structures such as altered DNA; and when a fluorescently stained biological sample is examined by fluorescence illumination the molecular structures can be seen, but the specific cell type or disease state cannot be directly observed. These characteristics along with other characteristics of fluorescence examination are discussed herein.

In fluorescence examination, the sample is stained with a fluorescent dye. A fluorescent dye has the ability to absorb light at one wavelength and emit light at a different wavelength. The resulting image when examined microscopically show bright fluorescence staining on a dark background. Typically, this type of stain would be used as a primary stain to visualize certain molecular structures. The sample could then be counterstained with a fluorescence counterstain to provide a nuclear counterstain.

Fluorescence staining is useful for identifying molecular structures within tissues. For example, genetic alterations at the level of the DNA can be examined. Furthermore, multiple different molecular alterations can be examined simultaneously by staining with two or more different fluorochromes that produce different colored signals. For example, in one common application, one molecular structure could be stained with the fluorochrome fluorescein which gives a green color, and another molecular structure could be stained with the fluorochrome rhodamine which gives a red color. Typically, the green fluorochrome emits light at about 590 nm and the red fluorochrome emits light at about 515 nm. Because these two wavelengths are commonly used for specific fluorescence staining, these wavelengths are reserved, meaning that any other stains or counterstains should not emit fluorescence at these wavelengths. In some instances, a fluorescence counterstain may be used but this is not always the case. In instances when a fluorescence counterstain is used the 4',6-diamidino-2-phenylindole (DAPI) counterstain is frequently chosen as it emits light in the blue spectrum at about 500 nm. When DAPI counterstain is combined with fluorescein and rhodamine the resulting stains will show a blue nuclear counterstain with specific green and red signals superimposed upon a dark background.

In addition to the DAPI counterstain, there are a number of other useful nuclear counterstains that can be used with fluorescence illumination. Each of these counterstains is able to bind to DNA thus staining the nucleus of cells and to emit light at various different wavelengths. Such counterstains may include the family of Hoechst stains (blue), propidium iodide (red), and Acridine Orange (Orange). In addition to the fluorochromes rhodamine and fluorescein, there are numerous other useful fluorochromes, such as the family of cyanine dyes. While many of these dyes are potentially useful, each dye requires a microscope with a specific filter set that can produce the required wavelengths for excitation and emission. Based on practical considerations most fluorescence microscopes are configured for green and red fluorescence, but may not be configured for other color combinations.

Combining Fluorescence Examination (Illumination) and Brightfield Examination (Illumination)

Currently, brightfield staining and examination are not combined with fluorescence staining and examination on one slide. Two separate slides are prepared from the same biological sample such that one slide can be fluorescently stained and examined and the other slide can be brightfield stained and examined. This method of staining two separate slides is time-consuming, expensive, and inaccurate, consequently there is a need to combine both types of staining and illumination on the same slide. Methods for combining both types of staining on a single slide by providing a counterstain that is useful in both brightfield and fluorescence modes is needed. This new counterstain and methods of using the counterstain would allow a microscopist to first examine a stained biological sample under brightfield illumination to obtain morphological information useful in identifying a cell type or disease state. Then, having established the cell type or disease state, the illumination source is switched from brightfield mode to fluorescence mode, and under this mode of illumination the molecular staining is now visible. In addition to the pathologist visualizing the sample under a microscope under two different modes of illumination, a digital image can be captured under each mode of illumination, and then digitally combined into a single composite image showing both morphological information regarding cell type or disease state and molecular information.

Described herein are combined counterstains and methods of using the combined counterstains to allow brightfield examination and fluorescence examination on a single slide. Currently, no brightfield counterstains have previously been identified that are useful in both brightfield and fluorescence illumination. Therefore, it would be very useful to identify one or more counterstains that could be used in both brightfield and fluorescence illumination.

For brightfield counterstains the criteria for selection are as follows: a counterstain must stain the nucleus without staining other cell or tissue elements; preferably the counterstain would be blue; the counterstain must be equivalent in quality to the conventionally used counterstains such as hematoxylin; and the counterstain must provide useful morphological information, such as the identification of cell types and disease states.

For fluorescence counterstains the criteria for selection are as follows: a counterstain cannot quench, interfere, or suppress specific fluorescence signals within the red and green spectrum; a counterstain cannot increase background or auto-fluorescence within the red or green spectrum; a counterstain cannot emit its own fluorescence within the red or green spectrum; a counterstain may emit its own fluorescence outside of the red or green spectrum thereby producing its own fluorescent counterstain; and in the absence of producing its own fluorescent counterstain, the counterstain can be combined with other desirable fluorescent dyes to produce a fluorescent counterstain, provided said counterstain does not fluoresce within the red and green spectrum.

What is needed are counterstains that can function as a combined brightfield and fluorescence counterstain. To function as a combined brightfield and fluorescence counterstain, the combined counterstain stain must have all of the following characteristics: the ability to be used as a nuclear counterstain by brightfield illumination; no fluorescence, or no fluorescence at wavelengths reserved for the desired fluorescence signal, when examined by fluorescence; no background fluorescence; and no interference or quenching of a desired fluorescence signal.

In addition, a combined counterstain can have an emission spectrum of about 400 to about 700 nm (entire visible spectrum) or an emission spectrum of about 400 nm to about 550 nm (blue spectrum).

Any existing counterstain that has the ability to bind selectively to DNA could conceivably have the ability to function as a brightfield nuclear stain. However, very few counterstains have the ability to function as both a brightfield and a fluorescence counterstain at the same time. Even if a counterstain does have the ability to selectively bind to DNA, several problems still exist: the counterstain interferes with a specific fluorescence stain by causing degradation of the desired fluorescence signal; the counterstain interferes with a desired fluorescence signal by causing an increase in nonspecific background fluorescence; the counterstain interferes with a desired specific fluorescence signal by producing fluorescence at the same wavelength as the desired fluorescence signal; and the counterstain cannot be combined with other fluorescent dyes to produce fluorescent nuclear staining of cells within a biological sample.

Combinations of Fluorescent Counterstains and Brighfield Counterstains

Chose one fluorescent counterstain and one brightfield counterstain. Examples of both types of counterstains are provided below.

Two combinations were tested; both can be used as a combination counterstain.

1. Hoechst 33342+Chicago Sky Blue (data not shown).

2. Hoechst 33342+Celestine Blue (results described herein).

Several of the compounds provided herein have an "x" in front of H20. In these structures and formulas, x is equal to, or greater than 0.

TABLE 1

| Group 1 - Fluorescent Counterstains | Group 2 - Brightfield Counterstains |
|---|---|
| Bisbenzimide-based counterstains | Chicago Sky Blue (Sigma Aldrich) CAS No. 2610-05-1 |
| Hoechst 33258 (Sigma-Aldrich) CAS Number: 23491-45-4 | Celestine Blue (Sigma Aldrich) CAS No: 1562-90-9 |
| Hoechst 33342 (Sigma-Aldrich) CAS Number: 23491-52-3 | Coerestin Blue CAS No. 1563-02-6 |
| Hoechst 34580 (Sigma-Aldrich) CAS Number: 911004-45-0 | |
| Hoechst 2495 (Sigma-Aldrich) CAS Number 72845-94-4 | |
| 2-phenylindole-based counterstains | |
| DAPI (Sigma-Aldrich) 4',6-diamidino-2-phenylindole CAS Number: 28718-90-3 | |

Conditions Tested for Dyes when Used Individually

TABLE 2

| Dye | Concentration | pH |
| --- | --- | --- |
| Hoechst 33342 | 2.5 µg/ml | 7.5 |
| Celestine Blue | 50 mg/ml | 3 |
| Chicago Sky Blue | 50 mg/ml | 3 |
| DAPI | 1.0 µg/ml | 7.5 |

Conditions Tested for a Mixture of Celestine Blue and Hoechst 33342

TABLE 3

| Mixture of Hoechst 33342 and Celestine Blue | Concentrations Tested | Optimal Concentration (other concentrations tested will also work though not as well) |
| --- | --- | --- |
| Celestine Blue Concentration (mg/ml) | 50 mg/ml, 40 mg/ml, 30 mg/ml, 20 mg/ml, 10 mg/ml | 20 mg/ml |
| Hoechst 33342 Concentration (ug/ml) | 2.5 ug/ml, 5 ug/ml, 10 ug/ml, 20 ug/ml, 40 ug/ml, 80 ug/ml | 20 ug/ml |
| pH of combined counterstain (Celestine Blue and Hoechst 33342) (0.15M citrate buffer) | pH 3, 3.5, 4, 4.5, 5, 5.5, 6, 6.5, 7, 7.5 | pH 6.0 pH 5.0 to 7.0 +/− 1 pH unit |

Fluorescent Counterstains Based on Bisbenzimide

Compound (I): bisbenzimide

Compound (I): C27H28N6O

Compound (I): 2'-(4-Ethoxyphenyl)-6-(4-methyl-1-piperazinyl)-1H,3'H-2,5'-bibenzimidazole A Compound of Formula (I):

Hoechst 33258

The following three chemical structures all have CAS No. 23491-45-4.

Compound (II): Bisbenzimide H 33258 Fluorochrome, Trihydrochloride

Compound (II): C25H24N6O.3HCl

Compound (II): 2-[2-(4-Hydroxyphenyl)-6-benzimidazoyl]-6-(1-methyl-4-piperazyl)-benzimidazole, 3HCl A Compound of Formula (II):

Bisbenzimide H 33258 Fluorochrome, Trihydrochloride is a membrane-permeant, adenine-thymidine specific fluorescent stain (excitation maximum: 346 nm; emission maximum: 460 nm) that is useful for staining DNA, chromosomes, and nuclei.

Compound (III): bisBenzimide H 33258≥98% (HPLC and TLC)

Compound (III): (Hill Notation) C25H24N6O.3HCl

Compound (III): 2'-(4-Hydroxyphenyl)-5-(4-methyl-1-piperazinyl)-2,5'-bi(1H-benzimidazole) trihydrochloride, 2-[2-(4-Hydroxyphenyl)-6-benzimidazoyl]-6-(1-methyl-4-piperazyl) benzimidazole trihydrochloride A Compound of Formula (III):

Molecular Weight 533.88
Excitation max.=346 nm
Emission max.=460 nm bisBenzimide H 33258 is useful for staining DNA, chromosomes and nuclei. bisBenzimide H 33258 may be used for fluorescence microscopy or flow cytometry. bisBenzimide H 33258 is a membrane-permeable, fluorescent DNA stain with low cytotoxicity that intercalate in A-T regions of DNA.

Compound (IV): Hoechst 33258 solution, 1 mg/mL in H2O, ≥98.0% (HPLC)

Compound (IV): (Hill Notation) C25H24N6O•3HCl

Compound (IV): 2'-(4-hydroxyphenyl)-5-(4-methyl-1-piperazinyl)-2,5'-bi-1H-benzimidazole trihydrochloride hydrate A Compound of Formula (IV):

Molecular Weight 533.88

Hoechst 33342

The following two chemical structures have CAS No. 23491-52-3.

Compound (V): Bisbenzimide H 33342 Fluorochrome, Trihydrochloride

Compound (V): $C_{27}H_{28}N_6O.3HCl$

Compound (V): 2'-(4-Ethoxyphenyl)-5-(4-methyl-1-piperazinyl)-2,5'-bi-1H-benzimidazole, 3HCl A Compound of Formula (V):

Bisbenzimide H 33342 Fluorochrome, Trihydrochloride is a cell-permeable, adenine-thymine-specific fluorescent stain that is useful for staining DNA, chromosomes, and nuclei for fluorescence microscopy and flow cytometry applications.

Compound (VI): bisBenzimide H 33342 trihydrochloride ≥98% (HPLC and TLC)

Compound (VI): (Hill Notation) $C_{27}H_{28}N_6O \cdot 3HCl \cdot xH_2O$

Compound (VI): 2-(4-Ethoxyphenyl)-5-(4-methyl-1-piperazinyl)-2,5-bi-1H-benzimidazole trihydrochloride A Compound of Formula (VI):

Molecular Weight 561.93 (anhydrous basis).

Useful for staining DNA, chromosomes and nuclei. May be used for fluorescence microscopy or flow cytometry.

Excitation max.=346 nm.

Emission max.=460 nm.

bisBenzimide H 33342 trihydrochloride can be used to study biochemicals and reagents, fluorescent probes, labels, particles and stains, luminescent compounds and detection and wavelength index.

Hoechst 34580

Compound (VII): HOECHST 34580 Trihydrochloride salt, ≥98.0% (HPLC)

Compound (VII): (Hill Notation) C27H29N7•3HCl

Compound (VII): N,N-Dimethyl-4-[5-(4-methyl-1-piperazinyl)[2,5'-bi-1H-benzimidazol]-2'-yl]benzenamine trihydrochloride

A Compound of Formula (VII):

CAS Number 911004-45-0
Molecular Weight 560.95
Hoechst 2495
Compound (VIII): HOECHST 2495
Compound (VIII): (Hill Notation) C24H29N3O12S2

Compound (VIII): Xanthane (2,1,9-def) isoquinolinedisulfonic acid, 2-(2-hydroxyethyl)-1,3-dioxo-, bis (2-ethanolamine) salt

A Compound of Formula (VIII):

Other Names: Benzoxanthene Yellow H 2495 Fluorochrome, Benzoxanthene Yellow H 2495, Benzoxanthene yellow
CAS Number 72845-94-4
Molecular Weight 615.63
Hoechst 2495
Compound (IX): HOECHST 2495
Compound (IX): C24H27N3O12S2

Compound (IX): Xanthane (2,1,9-def) isoquinolinedisulfonic acid, 2-(2-hydroxyethyl)-1,3-dioxo-, bis (2-ethanolamine) salt

A Compound of Formula (IX):

Molecular Weight 613.624
Fluorescent Counterstains Based on Phenylindole
Compound (X): 2-phenylindole
Compound (X): C14H11N Compound (X): 2-phenylindole

A Compound of Formula (X):

DAPI
Compound (XI): DAPI, suitable for fluorescence, ≥95.0% (HPLC)
Compound (XI): (Hill Notation) C16H15N5•2HCl Compound (XI): 4',6-Diamidino-2-phenylindole dihydrochloride A Compound of Formula (XI):

CAS Number 28718-90-3
Molecular Weight 350.25
Synonym: 2-(4-Amidinophenyl)-6-indolecarbamidine dihydrochloride, DAPI dihydrochloride DAPI may be used for photofootprinting of DNA, to detect annealed probes in blotting applications by specifically visualizing the double-stranded complex, and to study the changes in DNA and analyze DNA content during apoptosis using flow cytometry. DAPI staining has also been shown to be a sensitive and specific detection method for mycoplasma.
DAPI dilactate ≥98% (HPLC)
Compound (XII): DAPI dilactate ≥98% (HPLC)
Compound (XII): (Hill Notation) C16H15N5•2C3H6O3

Compound (XII): 4',6-Diamidino-2-phenylindole, dilactate

A Compound of Formula (XII):

Molecular Weight 457.48
A high sensitivity dye used to detect single nucleic acid molecules. DAPI has been shown to detect a single DNA molecule in solution, and to detect femtograms of DNA in single cells and chloroplasts.

DAPI Stain

Compound (XIII): DAPI STAIN

Compound (XIII): C16H15N5•2HCL

Compound (XIII): 4',6-Diamidino-2-phenylindole dihydrochloride

A Compound of Formula (XIII):

CAS Number 28718-90-3

A 5 mg/ml (14.27 mM) sterile-filtered solution of DAPI, 2HCl in $H_2O$.

Synonym: 2-(4-Amidinophenyl)-1H-indole-6-carboxamidine, 2HCl, 2-(4-Carbamimidoylphenyl)-1H-indole-6-carboximidamide, 2HCl, DAPI, ≥97% by HPLC, in H20

DAPI STAIN is a cell-permeable DNA-binding dye that binds preferentially to DNA rich in adenine and thymine. It is used in flow cytometry for measuring nuclear DNA content or for sorting isolated chromosomes. It is also useful for microscopic detection of nuclei and nuclear DNA in normal and apoptotic cells, and to detect *mycoplasma*.

Chicago Sky Blue

Compound (XIV): CHICAGO SKY BLUE

Compound (XIV): C34H24N6Na4O16S4

Compound (XIV): 6,6'-[(3,3-Dimethoxy[1,1'-biphenyl]-4,4'-diyl)bis(azo)]bis[4-amino-5-hydroxy-1,3-napthalenedisulphonic acid] tetrasodium A Compound of Formula (XIV):

CAS 2610-05-1

Molecular Weight: 992.80

Celestine Blue

Compound (XV): CELESTINE BLUE

Compound (XV): C17H18ClN3O4

Compound (XV): 1-carbamoyl-7-(diethylamino)-3,4-dihydroxyphenoxazin-5-ium chloride A Compound of Formula (XV):

PubChem 54684697

Molecular Weight: 363.798 g/mol

Chemical Name: CAS 1562-90-9

Compound (XVI): 7-(diethylamino)-3,4-dioxo-4,10-dihydro-3h-phenoxazine-1-carboxamide Compound (XVI): C17H17N3O4

Compound (XVI): 7-(diethylamino)-3,4-dioxo-4,10-dihydro-3h-phenoxazine-1-carboxamide A Compound of Formula (XVI):

Molecular Weight: 327.34 g/mol

Coerestin Blue

Compound (XVII): COERESTIN BLUE

Compound (XVII): C15H14ClN3O4

Compound (XVII): 7-(diethylamino)-4-hydroxy-3-oxophenoxazin-10-ium-1-carboxamide A Compound of Formula (XVII):

CAS 1563-02-6

Molecular Weight: 335.74

Variations of the disclosure include the discovery of new stains with the desirable characteristics mentioned above. There could also be the discovery that certain existing stains already exhibit the desirable characteristics listed above. Another variation would include the capture of digital images from the stained biological sample derived from a single microscope slide. The first image would include the image as seen under brightfield illumination. The second image would include the image as seen under fluorescence illumination. Using computer software, the two digital images would then be superimposed to produce a third composite image that contains the information derived from each separate image.

EXAMPLES

The following examples are intended to provide illustrations of the application of the present disclosure. The following examples are not intended to completely define or otherwise limit the scope of the disclosure. One of skill in the art will appreciate that many other methods known in the art may be substituted in lieu of the ones specifically described or referenced herein.

Example 1: Preparation of a Biological Specimen

A biological sample, for example a tissue biopsy, can be used to determine a disease state, such as the presence or absence of cancer. Such a determination requires that the tissue sample is first processed in a manner suitable for examination, and secondly, that a trained microscopist such as a pathologist performs the examination and renders a diagnosis.

The first step of this process involves preparing the tissue sample. Standard histological methods for tissue preparation include fixing the tissue in a chemical to render the sample metabolically inactive, preserve the morphological features of the tissue, and to stabilize the molecular structures. After fixation, the tissue is dehydrated in alcohol, cleared with a paraffin solvent such as xylene, and then submerged into melted paraffin. The melted paraffin then infiltrates the tissue, and upon cooling the tissue becomes embedded in a solid paraffin block. The paraffin block containing the tissue is then cut into thin sections using a microtome. One or more of the thin sections are then laid onto, and affixed to, a microscope slide.

The next step in the process is preparation for staining the tissue affixed to the slide. Before staining can commence the paraffin must be removed from the slide in a process call deparaffinization and rehydration. The slide is first exposed to a paraffin solvent such as xylene to remove all the paraffin. The slide is then exposed to alcohol to remove the paraffin solvent. The slides are then rehydrated by placing into an aqueous buffer solution to remove the alcohol and replace it with buffer.

The slide is now ready for staining. There are multiple types of different staining methods. These can be broken down into morphological stains, special stains, and molecular stains. The present disclosure deals primarily with morphological stains and molecular stains. Morphological stains are any stains that provide morphological information about the tissue, such as cell type, site of origin, and disease state. Typically, hematoxylin or hematoxylin and eosin are the morphological stains most commonly used.

The molecular stains may involve immunohistochemistry, which is a staining method used mainly to identify various protein molecules within the tissues. Most of the immunohistochemistry stains have been adapted for examination by brightfield illumination, although fluorescence illumination is sometimes used. Another type of molecular stain is in situ hybridization (ISH). Some of the ISH methods have been adapted to brightfield microscopy and are termed chromogenic in situ hybridization (CISH). However, the majority of ISH utilizes fluorescence illumination and is termed fluorescence in situ hybridization (FISH). The disclosed combination counterstains can be combined with any staining method that utilizes fluorescence illumination.

Example 2: Identification of a Combination Brightfield and Fluorescent Counterstain Breast cancer frequently presents with certain genetic defects that are most frequently identified by FISH methods. For example, amplification of the HER2 gene is seen in about 25% of breast cancer cases, and this amplification drives tumor development. If HER2 amplification is detected then the patient can benefit from certain treatments designed to interfere with HER2 signaling. On the other hand, if the tumor does not exhibit HER2 amplification, as is the case in about 75% of patients, then the patient would not benefit from HER2 targeted therapy. Thus, the proper determination of HER2 status is essential for proper treatment. In the FISH method of analysis, fluorescent probes are used that bind specifically to the HER2 gene. A normal cell would contain two copies of the HER2 gene, but an amplified cell would contain more than two copies of the gene. When the stained sample is viewed by fluorescence a number of small green dots within the cells will be apparent. If each cell contains two green dots, the gene is not amplified, but if each cell contains greater than two green dots, the gene is amplified. In addition to analyzing gene amplification, the FISH test also analyzes chromosome copy number. Again, a typical cell would contain two copies of each chromosome (chromosome 17 in the case of the HER2 gene). In the FISH test, each chromosome 17 is stained red. In certain cases of cancer, chromosome 17 may be either increased or decreased. By counting the number of red dots (chromosome 17) and green dots (HER2) a ratio is established between red and green. A ratio of green to red of greater than two indicates amplification of the HER2 gene.

To correctly evaluate the HER2 results by FISH it is necessary to stain a first slide with hematoxylin to identify the region of the tissue that contains the tumor cells. This slide is examined by brightfield illumination and those areas of the tissue that contain tumor cells are identified. A second serial section is then stained by FISH to identify HER2 genes (green) and chromosome 17 (red). Because the fluorescence slide does not contain morphological information, the microscopist must remember which area of the slide contained the tumor cells, and position the slide such that this area of the tissue is examined. If the tissue is not correctly positioned and the FISH analysis occurs on a portion of the tissue that does not contain tumor cells, the results will be inaccurate. Therefore, with this method of analysis there exists a possibility that the wrong part of the tissue is examined resulting in an incorrect result.

The present disclosure overcomes this limitation by performing both the morphological stain and the FISH stain on the same slide. To investigate the possibility of combining a brightfield and a fluorescence stain, numerous potentially useful counterstains were examined. A partial list of counterstains examined is shown in TABLE 2.

TABLE 2

List of Dyes Selected and Known Staining Characteristics.

| Dye | Color | Stain Location | Color in Brightfield | Color in Fluorescence |
|---|---|---|---|---|
| Alcian blue | blue | nuclear | blue | ? |
| Methyl blue | blue | nuclear | blue | ? |
| Methyl green | Green | Nuclear | Green | ? |
| Methylene blue | blue | nuclear | blue | orange |
| Toluidene blue | blue | nuclear | blue | no |
| Analine blue | blue | fat | blue | blue |
| Auramine O | ? | not nuclear | ? | blue |
| Azur A | red | not nuclear | red | ? |
| Azur B | blue | nuclear | ? | ? |
| Cresyl blue | blue | hemoglobin | blue | blue |
| Methyl violet | blue | nuclear | blue | ? |
| Hoechst | blue | ? | ? | blue |
| Nile Blue | blue | many | blue | orange |
| Crystal Violet | blue | nuclear | blue | ? |
| Celestine Blue | blue | nuclear | blue | ? |

The first step of this analysis consisted of collecting all known information about the selected group of counterstains; specifically, site of staining, color of stain by brightfield, and color of stain by fluorescence. This information, when available, was added to TABLE 2. As can be seen in TABLE 2, there was very little information available, particularly on the fluorescent properties of the dyes. Therefore, none of the selected dyes had sufficient information to predict which ones would most likely work. Therefore, these dyes were next examined to determine their fluorescence properties. Of the group of dyes examined, two appeared to fulfill the requirements for combined used in brightfield and fluorescence illumination methods. This dye were Methyl Green and Celestine Blue. The first of these dyes, Methyl Green, produced a green nuclear counterstain when examined by brightfield illumination, and was not further pursued as green was not a preferred color. The second of these dyes (Celestine Blue) produced a blue nuclear counterstain when viewed by brightfield illumination. Because of the desirability of the blue color, this dye (Celestine Blue) was tested further. The characteristics of Celestine Blue are as follows:

Brightfield Characteristics:
1. Blue nuclear counterstain. Does not stain any other cellular elements.

Fluorescence Characteristics:
1. Does not produce auto-fluorescence.
2. Does not quench, interfere, or otherwise decrease specific fluorescence signals in the green or red spectrum.
3. Does not emit its own fluorescence in the green or red spectrum.
4. Can be combined with other fluorescent dyes to produce a fluorescent nuclear counterstain. When combined with DAPI or Hoechst 33342 the combination produces a blue fluorescent counterstain with an emission of about 500 nm.

Example 3: Use of the Combined Brightfield and Fish Counterstain (Hoechst 33342 and Celestine Blue) for Identification of HER2 and Chromosome 17

The combined counterstain is a mixture of Hoechst 33342 (a fluorescent stain) and Celestine Blue (a brightfield stain). A tissue sample on a microscope slide was stained using the FISH method for HER2, resulting in specific FISH signals of green for HER2 and red for chromosome 17. The slide was also counterstained with Celestine Blue. The slide is first examined by brightfield illumination (FIG. 1 left-hand panel) where the blue nuclei are visible. Based on the nuclear morphology of the sample, the tumor component of the tissue was identified, and that portion of the tissue is positioned under the objective lens of the microscope. Without moving the slide, the illumination is switched from brightfield mode to fluorescence mode. Even though the morphology of the tissue is not directly observable the microscopist knows that the tumor portion is properly positioned because the slide has not been moved since properly positioned by brightfield illumination. Under fluorescence illumination (FIG. 1, right-hand panel), the green and red dots were observed and counted, a ratio of green to red was established, and a determination of amplification status was made. The possibility that the wrong area was chosen for FISH analysis has been completely eliminated by this method.

Figure 1:
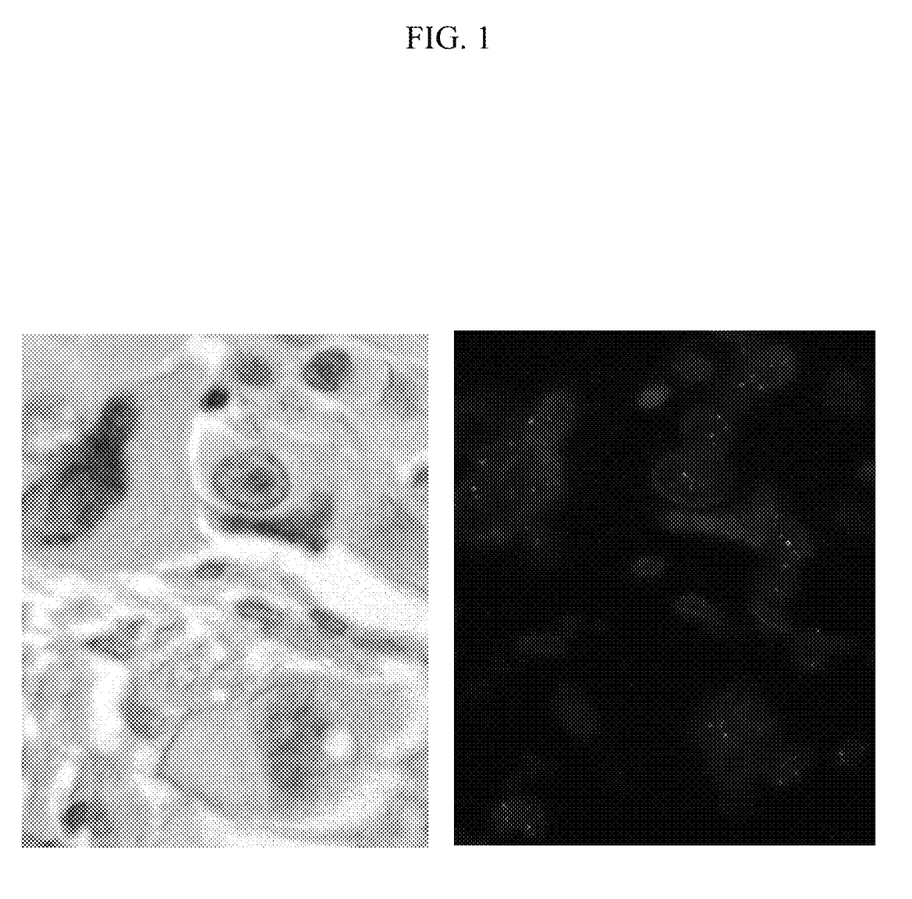
FIG. 1, left-hand panel shows a tissue sample stained with a combined counterstain of the disclosure under brightfield illumination.

FIG. 1, left-hand panel, shows HER 2 brightfield counterstain with Celestine blue. FIG. 1, right-hand panel, shows Hoechst nuclear counterstain 33342 (blue) centromere 17 (red) and HER2 gene (green).

Example 4: Use of the Combined Counterstain on Breast Cancer Tissue

The combined counterstain is a mixture of Hoechst 33342 (a fluorescent stain) and Celestine Blue (a brightfield stain). The tissue is a breast cancer specimen on a single slide. The slide is first examined by brightfield illumination where the blue nuclei are visible. Based on the nuclear morphology of the sample, the tumor component of the tissue was identified, and that portion of the tissue is positioned under the objective lens of the microscope. Without moving the slide, the illumination is switched from brightfield mode to fluorescence mode. Even though the morphology of the tissue is not directly observable the microscopist knows that the tumor portion is properly positioned because the slide has not been moved since properly positioned by brightfield illumination.

Figure 2:
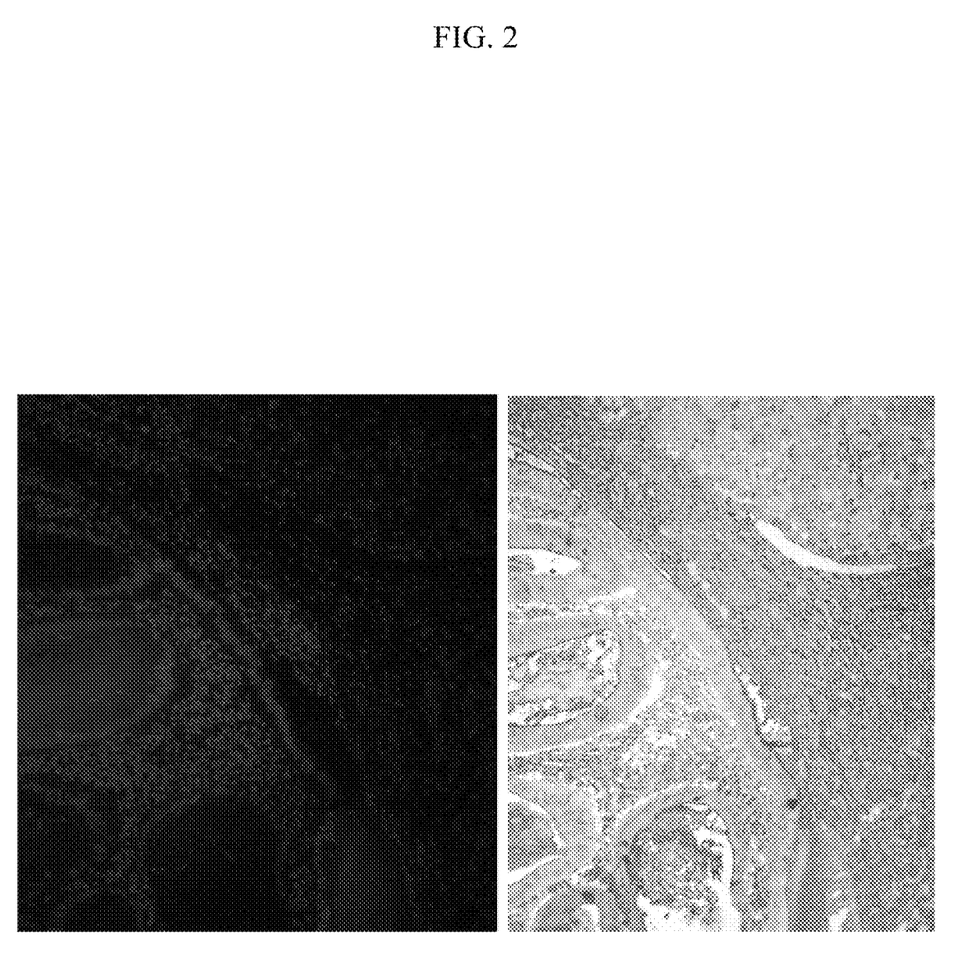
FIG. 2, left-hand panel shows a tissue sample stained with a combined counterstain of the disclosure under fluorescence illumination (low power).
Figure 3:
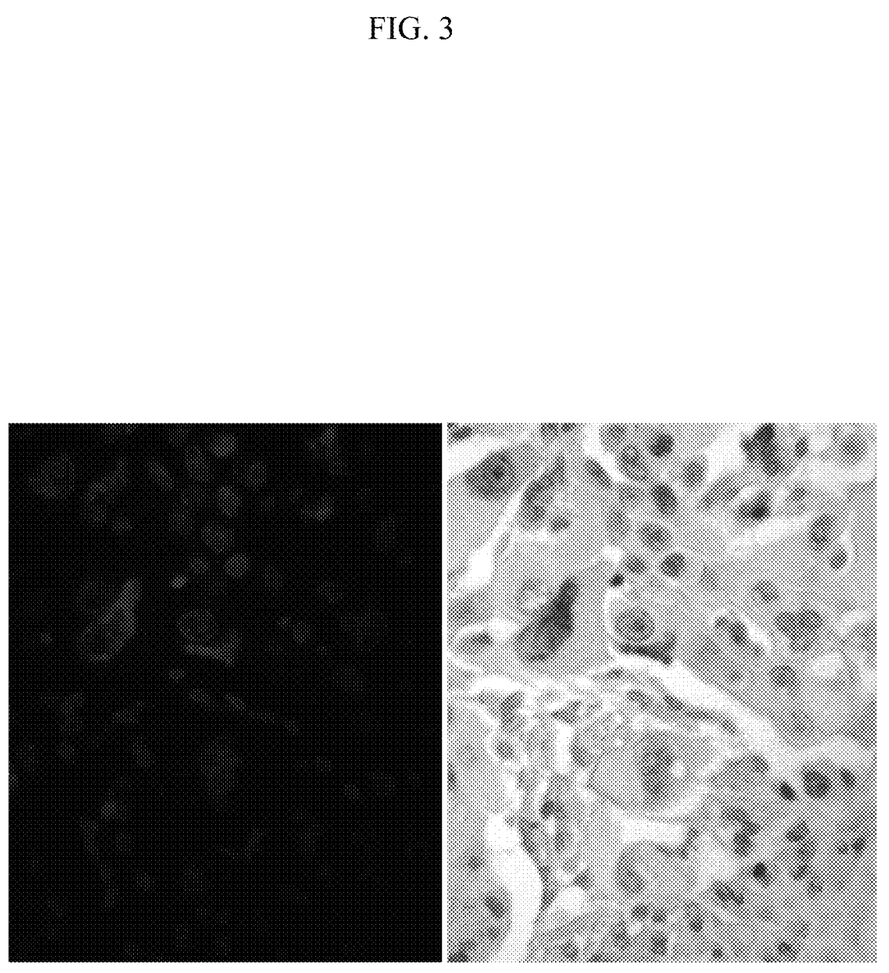
FIG. 3, left-hand panel shows the same tissue sample as FIG. 2 left-hand panel under fluorescence illumination (high power).

In FIG. 2, both the left-hand panel and the right-hand panel are the same slide and the same field of view. If the two images were superimposed the nuclei would line up exactly. FIG. 2, left-hand panel: low power, Hoechst 33342 fluorescent counterstain showing blue staining nuclei on a black background. FIG. 2, right-hand panel: low power, Celestine Blue brightfield counterstain showing blue staining nuclei on a light background. FIG. 3, left-hand panel: high power, same as FIG. 2, left-hand panel. FIG. 3, right-hand panel: high power, same as FIG. 2, right-hand panel. In FIG. 3, right-hand panel, the upper right corner shows predominantly breast cancer cells. This information can be used to analyze the same area in FIG. 2, left-hand panel.

Example 5: Colon Carcinoma Double Stained for Cytokeratin and IGG

Colon carcinoma was fixed in formalin and then embedded in paraffin using standard histological methods. Sections were cut at 4µ and mounted onto positively-charged microscope slides. Slides were deparaffinized and prepared for immunohistochemical staining. The first antibody was cytokeratin (clone AE1/AE3) which reacted with the epithelium of normal colon and colon carcinoma. The slides were next reacted with goat anti-mouse immunoglobulin polymer containing the enzyme alkaline phosphatase. Finally, the slides were then incubated with Fast Red/naphthol phosphate as the substrate for alkaline phosphatase. The red reaction product was visible in both brightfield illumination (FIG. 4, left-hand column, top and bottom images) and fluorescence illumination (FIG. 4, right-hand column, top and bottom images). The top row of each panel shows the tissue under high power, and the bottom row of each panel shows a different field of view under low power.

When the cytokeratin stain was completed, a second stain was performed using a mouse monoclonal antibody to IgG. After incubation with the anti-IgG was completed, the slides were then reacted with a goat anti-mouse immunoglobulin that was conjugated with the fluorescent dye, fluorescein isothiocyanate. Cells positive for IgG were stained green when viewed by fluorescence.

Slides were then counterstained in a mixture of Celestine Blue and Hoechst 33342. The finished slides were viewed microscopically with the following results. For brightfield illumination: nuclei were stained blue, cytokeratin was stained red, and IgG was not visible. For fluorescence illumination: nuclei were stained blue, cytokeratin was stained red, and IgG was stained green.

Figure 4:
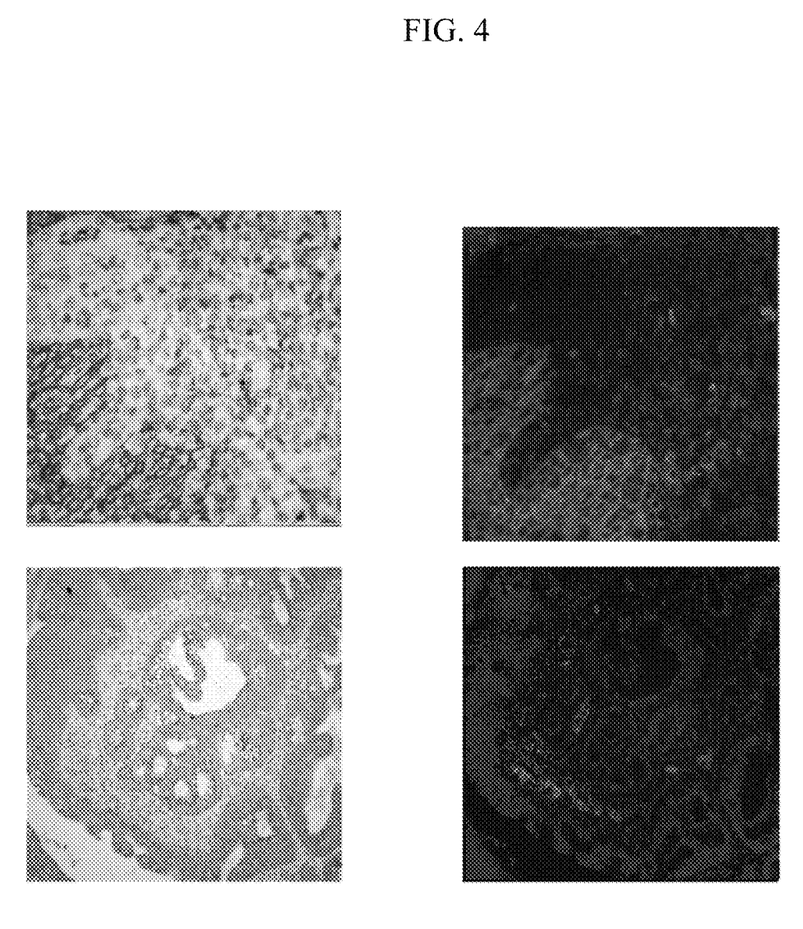
FIG. 4, left-hand panel (top and bottom) shows a tissue sample stained with a combined counterstain of the disclosure under brightfield illumination.

Specific IgG staining associated with colonic epithelium is an indication of certain inflammatory and/or autoimmune disorders, such as ulcerative colitis. As shown in FIG. 4, right hand column, the IgG staining (green) was not associated with colonic epithelium (red). This staining pattern was considered normal, and therefore, ulcerative colitis was ruled out of the diagnosis.

Example 6: Failure of Combined Hematoxylin and Hoechst 33342

Hematoxylin is one of the most widely used nuclear counterstains in histology for staining tissues and cells, so it would make sense to try this dye first. Hematoxylin stains the nucleus of cells blue when viewed by brightfield microscopy. Therefore, hematoxylin would be an ideal counterstain to combine with a fluorescent counterstain, such as Hoechst 33342. Unfortunately, as described below, it did not work because it caused quenching of the Hoechst dye.

Hematoxylin was obtained from Diagnostic Biosystems (cat. # K056). Hoechst 33342 was obtained from Sigma-Aldrich (cat. # B2261) and diluted to a concentration of 10 ug per mL in deionized water.

Hematoxylin was mixed with Hoechst 33342 at a ratio of 1:1. The resultant dye mixture was used to stain a tonsil tissue section. The tissue section was stained for 5 minutes in the dye mixture and then rinsed in deionized water. The stained tissue sections were then mounted in an aqueous mounting medium and coverslipped with a glass coverslip in preparation for microscopic analysis. When viewed by brightfield illumination the nuclei of the lymphocytes were stained blue. However, when viewed by fluorescence illumination no staining of lymphocytes was observed. These findings showed that it was not possible to mix hematoxylin with certain fluorescent dyes to achieve a mixed dye displaying both brightfield and fluorescence characteristics.

The inability to observe any fluorescence counterstain in the mixed dye could have been due to the fact that the hematoxylin displaced or competed with Hoechst for binding sites, thus preventing Hoechst from binding to the nuclei. Alternatively, the hematoxylin may have absorbed the fluorescence emissions from the Hoechst dye, thus preventing their detection.

After staining with the mixed dye, as described above, the coverslips were removed from the tissue sections and the sections were rehydrated in water. Next the slides were decolorized in a solution of 95% alcohol and 5% 0.2M citric acid. The decolorization procedure gradually removed the hematoxylin from the tissue section. As the hematoxylin was removed, the Hoechst stain became visible. These results indicate that Hoechst dye had indeed bound to the tissue section but was not detectable due to quenching by the hematoxylin. As the hematoxylin was removed the bound Hoechst was once again visible under fluorescence illumination.

These results show that not all combinations of brightfield dyes and fluorescent dyes can be successfully combined. Indeed, only a very few combinations, as described herein, have been found to yield both fluorescence and brightfield characteristics.

While certain embodiments have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure. It is intended that the following claims define the scope of the disclosure and that methods and structures within the scope of these claims and their equivalents be covered thereby.

What is claimed is:

1. A method of staining a first section of a biological specimen on a first slide, wherein the first section is analyzed by microscopic analysis using both brightfield and fluorescent illumination, the method comprising the following steps:
   a) mounting the first section of the biological specimen onto the first slide;
   b) contacting the first section on the first slide with a first nuclear counterstain represented by the following structure:

wherein the first nuclear counterstain binds DNA within the first biological specimen and reflects visible light when examined by brightfield illumination;
   c) contacting the first section on the first slide with a first fluorescent dye that is a bisbenzimide dye, the first fluorescent dye binding to cellular components within the first biological specimen and to absorbing light at a first wavelength and emitting light at a different second wavelength;
   d) placing the first slide comprising the first section, the first nuclear counterstain, and the first fluorescent dye in a first position under view of a microscope that has both brightfield and fluorescent iliumination;
   e) viewing both the DNA stained with the first nuclear counterstain and the cellular components stained with the first fluorescent dye on the first slide by turning the microscope to brightfield illumination and then turning the microscope to fluorescent illumination while leaving the first slide in the same first position.

2. The method of claim 1, wherein the observation is by a person's eye.

3. The method of claim 1, wherein the first fluorescent dye produces one of a red stain and a green stain when viewed under fluorescence.

* * * * *